United States Patent
Evans et al.

(10) Patent No.: US 10,890,595 B2
(45) Date of Patent: Jan. 12, 2021

(54) METHOD AND APPARATUS FOR PRE-POSITIONING A RADIALLY SYMMETRIC, COAXIAL SAMPLE WITHIN A SHEATH FLUID TO PROVIDE UNIFORM SAMPLE DELIVERY RATE DURING FLOW

(71) Applicant: VISIONGATE, INC., Phoenix, AZ (US)

(72) Inventors: Nathaniel Evans, Redmond, WA (US); Jon W. Hayenga, Redmond, WA (US)

(73) Assignee: VISIONGATE, INC., Phoenix, AZ (US)

(*) Notice: Subject to any disclaimer, the term of this patent is extended or adjusted under 35 U.S.C. 154(b) by 245 days.

(21) Appl. No.: 15/782,760

(22) Filed: Oct. 12, 2017

(65) Prior Publication Data

US 2019/0113535 A1 Apr. 18, 2019

(51) Int. Cl.

| | | |
|---|---|---|
| *G01N 1/10* | (2006.01) | |
| *G01N 35/10* | (2006.01) | |
| *B01L 3/00* | (2006.01) | |
| *G01N 15/14* | (2006.01) | |
| *G01N 21/01* | (2006.01) | |
| *G01N 21/17* | (2006.01) | |
| *G01N 33/487* | (2006.01) | |

(52) U.S. Cl.
CPC ...... *G01N 35/1011* (2013.01); *B01L 3/50273* (2013.01); *B01L 3/502715* (2013.01); *B01L 3/502761* (2013.01); *B01L 3/502776* (2013.01); *G01N 15/1404* (2013.01); *G01N 21/01* (2013.01); *G01N 21/17* (2013.01); *G01N 33/4875* (2013.01); *G01N 35/1016* (2013.01); *B01L 2200/0652* (2013.01); *B01L 2200/0689* (2013.01); *B01L 2300/0832* (2013.01); *B01L 2400/0406* (2013.01); *B01L 2400/0478* (2013.01); *G01N 2015/1413* (2013.01); *G01N 2021/1787* (2013.01)

(58) Field of Classification Search
CPC ............... G01N 2015/1486; G01N 35/00584
USPC ....................... 436/179, 180, 174
See application file for complete search history.

(56) References Cited

U.S. PATENT DOCUMENTS

| | | |
|---|---|---|
| 5,785,926 A | 7/1998 | Seubert et al. |
| 6,027,682 A | 2/2000 | Almquist et al. |
| 6,050,450 A | 4/2000 | Gardos |
| 6,190,616 B1 | 2/2001 | Jovanovich et al. |
| 6,355,164 B1 | 3/2002 | Wendell et al. |
| 7,610,942 B2 | 11/2009 | Harui et al. |
| 7,867,778 B2 | 1/2011 | Hayenga et al. |
| 2005/0129795 A1 | 6/2005 | Farnworth |
| 2006/0052723 A1 | 3/2006 | Roe |
| 2011/0306031 A1* | 12/2011 | Rich .................. G01N 15/1404 435/3 |
| 2016/0368009 A1 | 12/2016 | Hatton et al. |

OTHER PUBLICATIONS

International App. No. PCT/US18/55665, International Search Report, dated Jan. 28, 2019.
International App. No. PCT/US18/55665, Written Opinion of the International Searching Authority, dated Jan. 28, 2019.

* cited by examiner

*Primary Examiner* — Natalia Levkovich
(74) *Attorney, Agent, or Firm* — George A. Leone; Citadel Patent Law

(57) ABSTRACT

A method for pre-positioning a coaxial sample and sheath combination includes calculating a load shape profile including a plurality of layers of substantially equal volume. The calculated load shape profile is incrementally divided into cross-sectional slices at a first set of distance coordinates along a first axis. Each cross-sectional slice transects the plurality of layers. A sample includes a number of objects residing in solution. A sample chamber is loaded with the sample by incrementally dispensing the sample in a plurality of portions along a vertical axis divided into a second set of distance coordinates proportional to the first set of distance coordinates, where each portion has a volume proportional to the cross-sectional slice at the first distance coordinate nearest in value to the second distance coordinate.

4 Claims, 11 Drawing Sheets

METHOD AND APPARATUS FOR PRE-POSITIONING A RADIALLY SYMMETRIC, COAXIAL SAMPLE WITHIN A SHEATH FLUID TO PROVIDE UNIFORM SAMPLE DELIVERY RATE DURING FLOW

TECHNICAL FIELD

The present invention relates to optical tomography on a cellular and sub-cellular scale. More particularly, the invention relates to a method and apparatus for loading sample into a chamber to achieve hydrodynamic focusing by pre-positioning target objects.

BACKGROUND

Lung cancer is the second most prevalent cancer in the United States and is the most lethal. Over 31 million patients in the United States (US) are at high risk for the development of lung cancer, primarily due to age, smoking history, pollution and other factors including radon exposure, family history of lung cancer, etc. Approximately 160,000 US patients die of lung cancer each year. At the time of this writing, lung cancer can only be cured with surgery when detected in early stages, mainly stage I and II. However, lung cancer is known to be preceded by pre-cancerous conditions presenting as dysplastic cells. The detection of such pre-cancerous conditions can trigger preventative treatment that can reduce the risk of contracting lung cancer.

Advances in 3D imaging of biological cells using optical tomography have been deployed by Nelson as disclosed, for example, in U.S. Pat. No. 6,522,775, issued Feb. 18, 2003, and entitled "Apparatus and Method for Imaging Small Objects in a Flow Stream Using Optical Tomography," the full disclosure of which is incorporated by reference. Further major developments in the field are taught in Fauver et al., U.S. Pat. No. 7,738,945, issued Jun. 15, 2010, entitled "Method and Apparatus for Pseudo-Projection Formation for Optical Tomography," (Fauver '945) and Fauver et al., U.S. Pat. No. 7,907,765, issued Mar. 15, 2011, entitled "Focal Plane Tracking for Optical Microtomography," (Fauver '765) the full disclosures of Fauver '945 and Fauver '765 are also incorporated by reference. Building on the teachings therein, an early lung cancer detection technology has been fully developed and commercialized by VisionGate, Inc., Phoenix, Ariz. to provide measurement advantages that have demonstrated a great improvement in the operating characteristics of conventional morphologic cytology analyses.

Processing in such an optical tomography system begins with specimen collection and preparation. For diagnostic applications in lung disease, patient sputum can be collected non-invasively in a clinic or at home. At the clinical lab, the sputum is processed to remove non-diagnostic material, fixed and then stained. Stained specimens are then mixed with an optical oil, and the suspension is injected into the storage chamber of a microfluidic pumping device referred to as the Prepjet™ device. The Prepjet™ device is installed on a Cell-CT™ platform and objects are pumped into a microcapillary tube, wherein the objects can be imaged. Images of objects, such as cells, in the specimen are collected while the cells are rotated around 360-degrees relative to the image collection optics in an optical tomography system. The resultant images comprise a set of extended depth of field images from differing perspectives called "pseudo-projection images." The set of pseudo-projection images can be mathematically reconstructed using backprojection and filtering techniques to yield a 3D reconstruction of a cell of interest. Having isometric or roughly equal resolution in all three dimensions is an advantage in 3D tomographic cell imaging, especially for quantitative feature measurements and image analysis.

The 3D reconstructed digital image then remains available for analysis in order to enable the classification through the measurement of sub-cellular structures, molecules or molecular probes of interest. An object such as a biological cell may be stained or labeled with at least one absorbing contrast agent or tagged molecular probe, and the measured amount and structure of this biomarker may yield important information about the disease state of the cell, including, but not limited to, various cancers such as lung, breast, prostate, cervical, stomach and pancreatic cancers, and various stages of dysplasia.

One challenge of current designs relates to optimizing throughput to reduce the time needed to image, reconstruct and analyze a sample. In an ideal system, optimized target object throughput would include uniform object rate delivery, dynamically focusing target objects, creating sheath fluid, automation of the sample preparation process and viscosity modulation. If not properly dispensed, highly undesirable clumps of target objects can form by object adherence to interfacial surfaces such as walls, other objects and diameter changes.

However, until the disclosure herein, there was no reliable method for preloading a coaxial sample and sheath combination with a sample having a core profile that allows an improved, nearly optimal, time of flight for the target objects from sample chamber to an imaging zone within a capillary. Before preloading, an improved core shape and position for the sample within the sheath can be developed to enhance throughput in an imaging flow cytometer using the method and apparatus disclosed herein.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

A method for pre-positioning a coaxial sample and sheath combination, is disclosed including the acts of calculating a load shape profile including a plurality of layers of substantially equal volume; incrementally dividing the calculated load shape profile into a plurality of cross-sectional slices of a predetermined thickness at a first plurality of distance coordinates along a first axis, wherein each cross-sectional slice transects the plurality of layers; obtaining a sample wherein the sample includes a plurality of objects residing in solution; and loading a sample chamber with the sample by incrementally dispensing the sample in a plurality of portions along a vertical axis divided into a second plurality of distance coordinates proportional to the first plurality of distance coordinates, where each portion has a volume proportional to the cross-sectional slice at the first distance coordinate nearest in value to the second distance coordinate.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 4A schematically shows a side view of a motor control unit and a precision sample dispenser.

Figure 1:
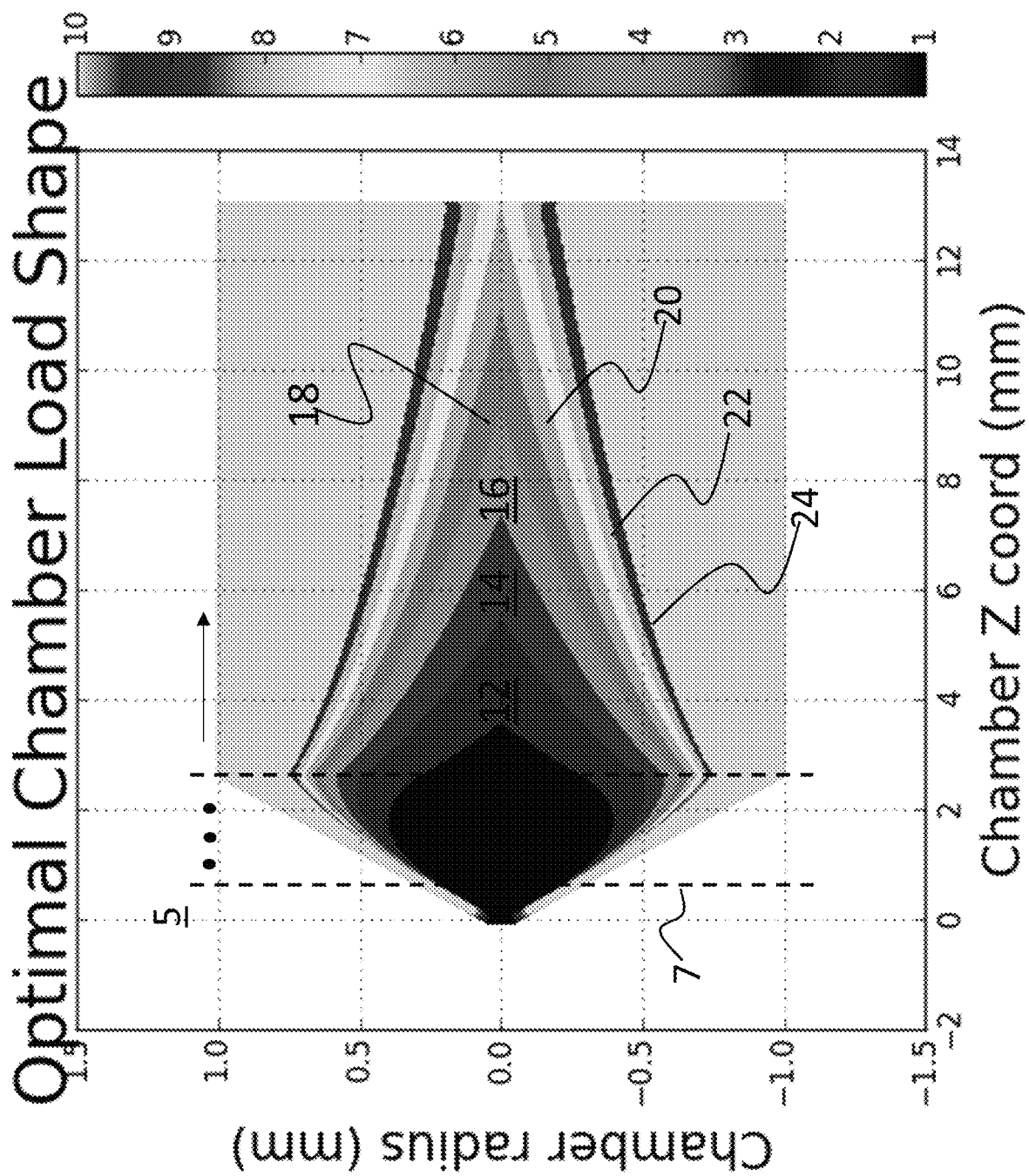
FIG. 1 graphically represents a hypothetical example of an optimal optical chamber load shape for loading a sample into a capillary.

In the drawings, identical reference numbers call out similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not necessarily intended to convey any information regarding the actual shape of the particular elements, and have been solely selected for ease of recognition in the drawings.

DETAILED DESCRIPTION OF THE PREFERRED EMBODIMENTS

The following disclosure describes a method and apparatus for precisely dispensing a sample into a receptacle used in an optical tomography cell imaging system. Several features of methods and apparatus in accordance with example embodiments are set forth and described in the figures. It will be appreciated that methods and apparatus in accordance with other example embodiments can include additional procedures or features different than those shown in the figures. Example embodiments are described herein with respect to loading sample into a chamber to achieve hydrodynamic focusing by pre-positioning target objects. However, it will be understood that these examples are for the purpose of illustrating the principles, and that the invention is not so limited.

Definitions

Generally, as used herein, the following terms have the following meanings, unless the use in context dictates otherwise:

The use of the word "a" or "an" when used in conjunction with the term "comprising" in the claims or the specification means one or more than one, unless the context dictates otherwise. The term "about" means the stated value plus or minus the margin of error of measurement or plus or minus 10% if no method of measurement is indicated. The use of the term "or" in the claims is used to mean "and/or" unless explicitly indicated to refer to alternatives only or if the alternatives are mutually exclusive. The terms "comprise", "have", "include" and "contain" (and their variants) are open-ended linking verbs and allow the addition of other elements when used in a claim.

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Adequacy" refers to the content of the specimen and defines a limit for target cells to determine if a sufficient cellular pellet has been analyzed.

"Capillary tube" has its generally accepted meaning and is intended to include transparent microcapillary tubes and equivalent items with an inside diameter generally of 500 microns or less, but larger diameters could be used.

"Capillary radius" means the radius of an object as referenced to the axial center locus of a capillary tube.

"Cell" means biological cell such as a human, mammal or animal cell.

"Cell-CT™ platform" refers to an optical tomography system manufactured by VisionGate, Inc. of Phoenix, Ariz. incorporating teachings of the Nelson and Fauver patents referenced herein above and improvements of those teachings.

"Depth of field" is the length along the optical axis within which the focal plane may be shifted before an unacceptable image blur for a specified feature is produced.

"Enrichment" refers to the process of extracting target cells from a raw specimen. The process yields an enriched pellet whose cells can then be more efficiently imaged on the Cell-CT™ platform.

"LuCED® test" refers to an early lung cancer detection test employing the Cell-CT™ platform as developed by VisionGate, Inc. of Phoenix, Ariz. incorporating the teachings of the Nelson and Fauver patents referenced hereinabove and improvements of those teachings.

"The LuCED® process" refers to the mechanism of 3D cell reconstruction, classification to find abnormal cells, and pathology confirmation.

"Object" means an individual cell, human cell, mammal cell, item, thing or other entity.

"Pseudo-projection" includes a single image representing a sampled volume of extent larger than the native depth of field of the optics where pseudo-projection image thus formed include an integration of a range of focal plane images from a fixed viewpoint. The concept of a pseudo-projection is taught in Fauver '945.

"Specimen" means a complete product obtained from a single test or procedure from an individual patient (e.g., sputum submitted for analysis, a biopsy, or a nasal swab). A specimen may be composed of one or more objects. The result of the specimen diagnosis becomes part of the case diagnosis.

"Sample" means a finished cellular preparation that is ready for analysis, including all or part of an aliquot or specimen.

"Subject" as used herein means a human patient.

"Target Cell" refers to a cell from a specimen whose characterization or enumeration is especially desired. For example, in the LuCED® test, the target cells are normal bronchial epithelial cells. A minimum number of these must be enumerated during the test in order for a specimen to be considered as adequate.

"Tear shaped," as used herein, has its generally accepted meaning, that is, shaped like a falling drop of a liquid, having a globular form at the bottom tapering to a point at the top.

"Threshold" as used in the context of image processing includes a decision boundary value for any measurable characteristic of a feature. Thresholds may be predetermined or set according to instrument specifications, acceptable error rates, statistics, or other criteria according to accepted pattern recognition principles.

"Voxel" as used in the context of image processing is a volume element on a 3D grid.

Referring to FIG. 1, an example of a hypothetical optimal optical chamber load shape for loading a sample into a capillary is illustrated. A load shape profile in its initial condition 5 is the volume that is first loaded into a sample chamber for subsequent introduction into a capillary tube. Applications of this technique may include introducing the sample into a sheath fluid volume to avoid target object contact with interfacial regions.

In one example, the load shape profile 5 includes a plurality of layers 10, 12, 14, 16, 18, 20, 22 and 24 each represent substantially the same amount of sample, for example, 1 µL-3.5 µL of sample. In one useful example the total amount of sample may be no more than 15 µL. The horizontal axis represents the chamber Z coordinate in millimeters (mm) ranging from −2 to 14 mm and the vertical axis represents the chamber radius in millimeters ranging from −1.5 to 1.5 mm. In an ideal process, each layer 10-24 is shaped to be injected into a chamber for loading a sample tube, such as, for example, a capillary tube.

Still referring to FIG. 1, a first generally tear shaped region 10 extends along the z-axis of a chamber, as described below, from a first end at a zero coordinate that is nearest an output port or nozzle as described below, a Z coordinate of about 4 mm. With respect to the chamber radius, the first region 10 has a width of about 0.8 mm centered symmetrically around a chamber radius coordinate of 0 mm. The next layer 12 extends to a Z coordinate of a little less than 6 mm and surrounds the first region 10 with a width extending from −0.5 mm to 0.5 mm as projected on the chamber radius axis. The layers from 14 through 24 all progress similarly having progressively thinner layers that extend farther along the Z coordinate of the chamber.

The load shape profile 5 models the time of flight for fluid locations within the chamber holding the sample and sheath fluid. By knowing the time of flight for the fluid it is possible to map the positions within the sample chamber that will be most advantageous for placing the sample within the sheath fluid for minimum run time in an optical tomography system. Note that the load shape profile 5 need not resemble a tear drop shape, but can be any geometric shape corresponding to a geometric shape of a sample chamber. For example, it may be a spike shaped profile or the like.

Figure 7:
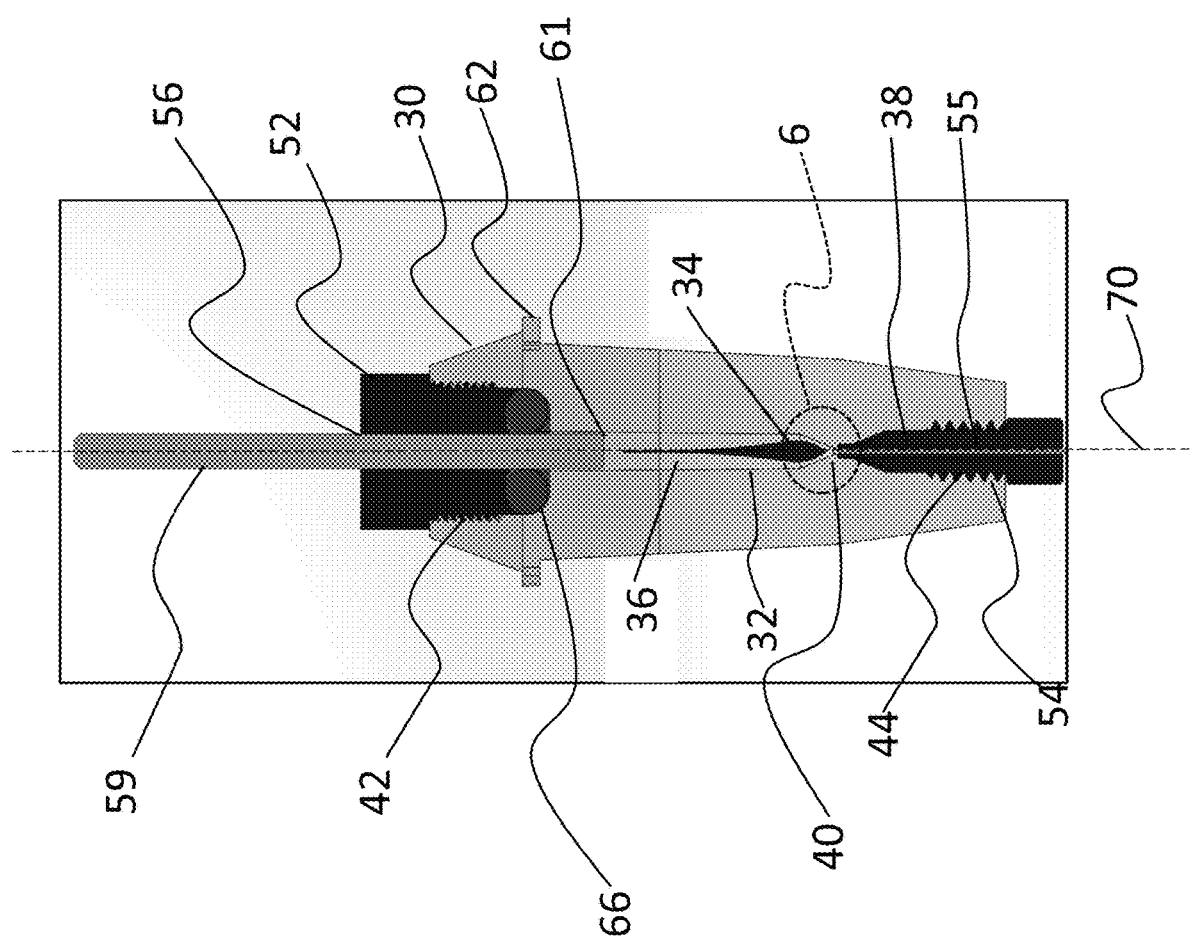
FIG. 7 conceptually shows a cross-sectional view of an example of a Prepjet™ focus cone body nozzle with a precision dispensed sample profile visualized as a tear drop shape in an inner bore.

Still referring to FIG. 1, in one example, the load shape profile 5 is dispensed as a series of cross-sectional slices 7 of a predetermined thickness when sample is dispensed into a sample chamber (as shown in FIG. 7, for example). In this way, a number of layers having a volume calculated from the profile of the load shape profile 5 is dispensed in steps. In one example, about 52 cross-sectional slices 7 may advantageously be incrementally dispensed with each cut displaced about 0.762 µm from the previous slice. Other increments may be employed. In selecting the increments, the trade-off is between more closely approximating an optimal load shape by taking cross-sections at smaller increments vs. the amount of time it takes to dispense the sample. The cross-section increments are controlled by operation of a stepping motor moving a syringe plunger as described below.

Figure 2:
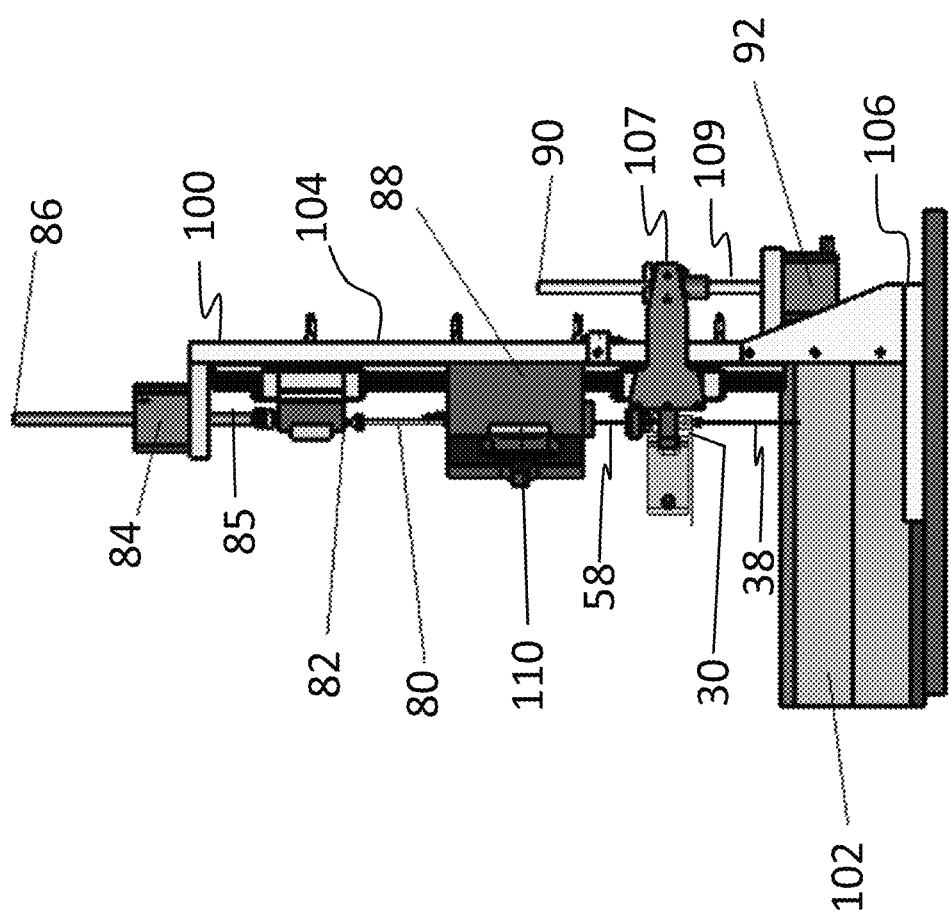
FIG. 2 schematically shows a side view of a motor control unit and injection device.

Referring now to FIG. 2, a side view of a motor control unit and injection device is schematically shown. An injection device 100 includes a first adjustment knob 86, a first motor 84, a plunger drive plate 82, a syringe fixture 88, a second adjustment knob 90, a second motor 92, a vertical mounting fixture 104 and a mounting plate 106. The plunger drive plate 82 is coupled to be raised and lowered by the first motor driveshaft 85. Similarly, a focus cone body holder 107 is coupled to a driveshaft 109 of the second motor 92.

Figure 3:
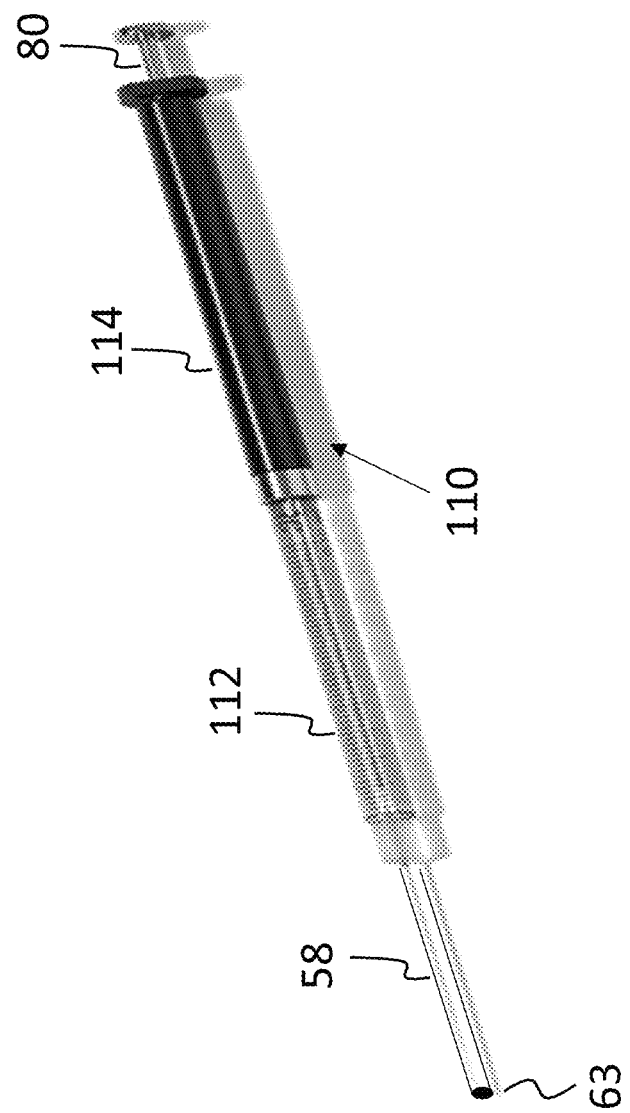
FIG. 3 schematically shows a syringe with a removable plunger support.

Referring now jointly to FIG. 2 and FIG. 3, a syringe 110 includes a hollow syringe needle 58, a barrel 112, a syringe holder 114 and a plunger 80 all concentrically aligned around a central axis. As shown in FIG. 2, the syringe 110 is mounted within the syringe fixture 88 with the plunger 80 extended and the barrel 112 preloaded with a sample. The sample preferably contains objects such as human cells and/or wafers embedded in media and intended to be dispensed into a focus cone body 30 having a sample storage region 32 (as best shown in FIG. 7). A capillary tube 38 is tightly held by the focus cone body 30.

In one example, a 100 µL syringe filled with a target object embedded optical media was effectively fitted with a blunt 22s gauge 2" needle. Of course, the invention is not so limited and the size of the syringe and syringe needle depends upon the particular application and those skilled in the art and having the benefit of this disclosure are capable of selecting an appropriate size.

A motor control unit 102 is electrically coupled to control both the first and second motors. When the syringe is mounted on the injection device, the plunger drive plate 82 bears against the plunger 80. The first motor 84 is mechanically connected to a shaft for vertically driving the plunger drive plate 82 which then presses the plunger 80. The second motor 92 operates to move the sample chamber transversely relative to the syringe needle 58 in a highly-controlled manner in order to dispense sample from the syringe into the sample chamber in preselected cross-sectional increments as described above with reference to FIG. 1.

Figure 4:
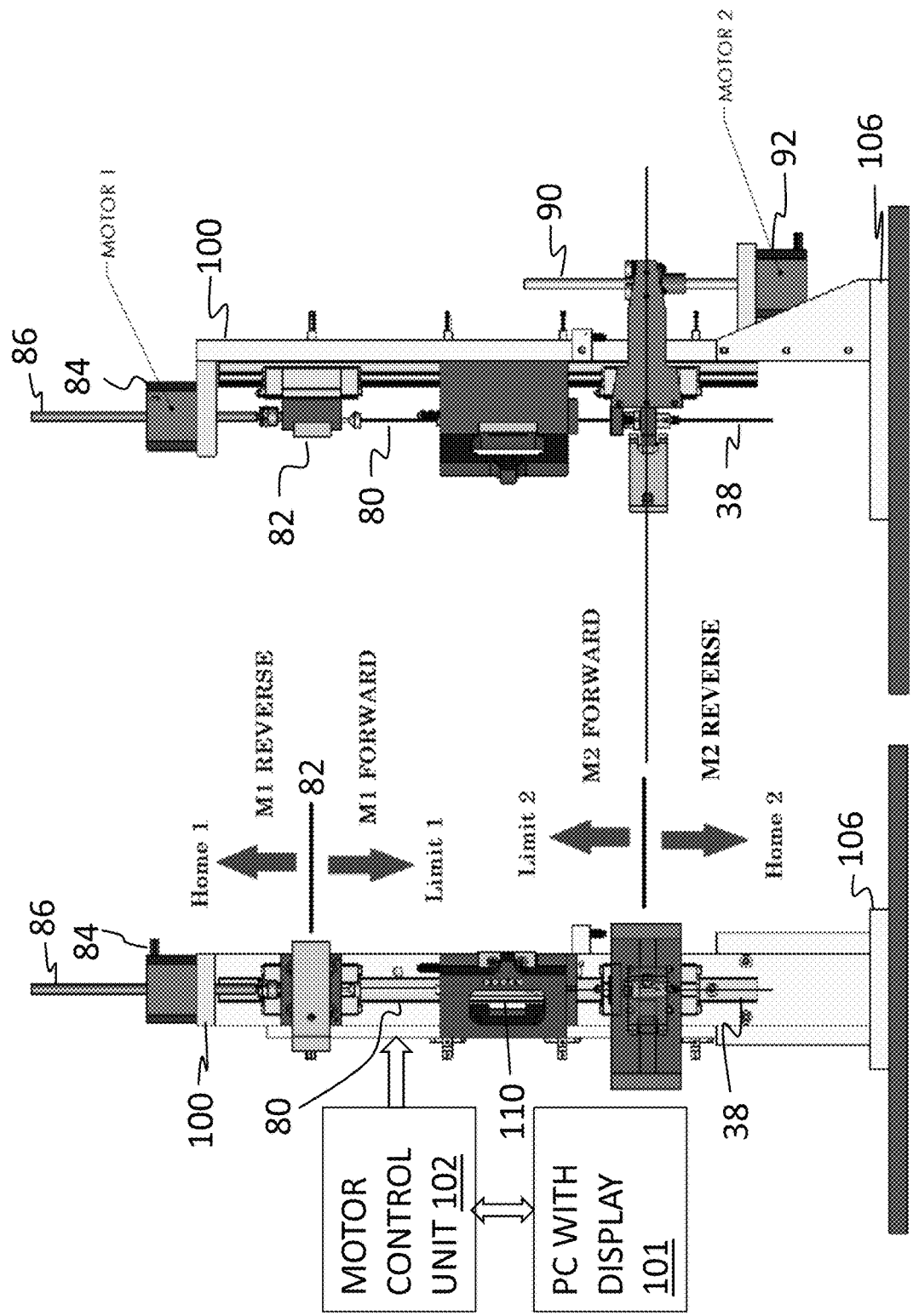
FIG. 4 schematically shows a front view of a motor control unit and a precision sample dispenser.

Referring now jointly to FIG. 4 and FIG. 4A, a front view of a motor control unit and a precision sample dispenser and a side view of a motor control unit and a precision sample dispenser are respectively shown. The motor control unit 102 is electronically coupled to the first motor 84 and the second motor 92 and supplies separate control signals to each. The motor control unit 102 is also advantageously coupled to a computer with a display for providing added control and security. Further, the motor control unit 102 may include its own processor for accepting commands from the computer and providing control signals to the first motor. A plurality of electrical-mechanical switches may also be included on the motor control unit for manual control of the motors, supplemental controls and/or substituting for or overriding the computer controls. The motor control unit may also be equipped with visual readout devices such as lights or meters as desired.

In one example, the user interface may include identification text boxes and the like, including passwords for security purposes. Barcode readers may also be used to scan the session numbers and the like, identifying a sample, for example. The injection device 100 may be provided with electronic or physical limit devices so that the first motor 86 is constrained between a first limit, "Home 1" in a reverse direction and "Limit 1" in a forward direction. Similarly, the second motor 92 is constrained between limits "Limit 2" in a forward direction and "Home 2" in a reverse direction. In one useful example, the limits are set using limit switches, such as miniature electronic switches or the like.

In operation, in one example, an operator will execute the following steps. The first motor 84 raises the plunger drive plate high enough to allow installation of the syringe plunger. The second motor 92 lowers the focus cone body holder 107 to enable installation of the syringe without the syringe needle and needle guide interfering. The first adjustment knob 86 is turned to raise the plunger drive plate. The second adjustment knob 90, or a computer jog control may be used to lower the second motor 92. To avoid contamination of samples it is important to use a new and clean needle guide when a syringe is loaded. When the first and second motors respectively move the plunger plate and the focus cone body holder in retracted positions, the needle guide and syringe may be installed. The second motor 92 may raise the focus cone body holder until the needle appears about ¼" below the bottom edge of the needle guide. This may be done by controlling the second motor drive screw either manually using the adjustment knob 90 or through the motor control unit.

Figure 5:
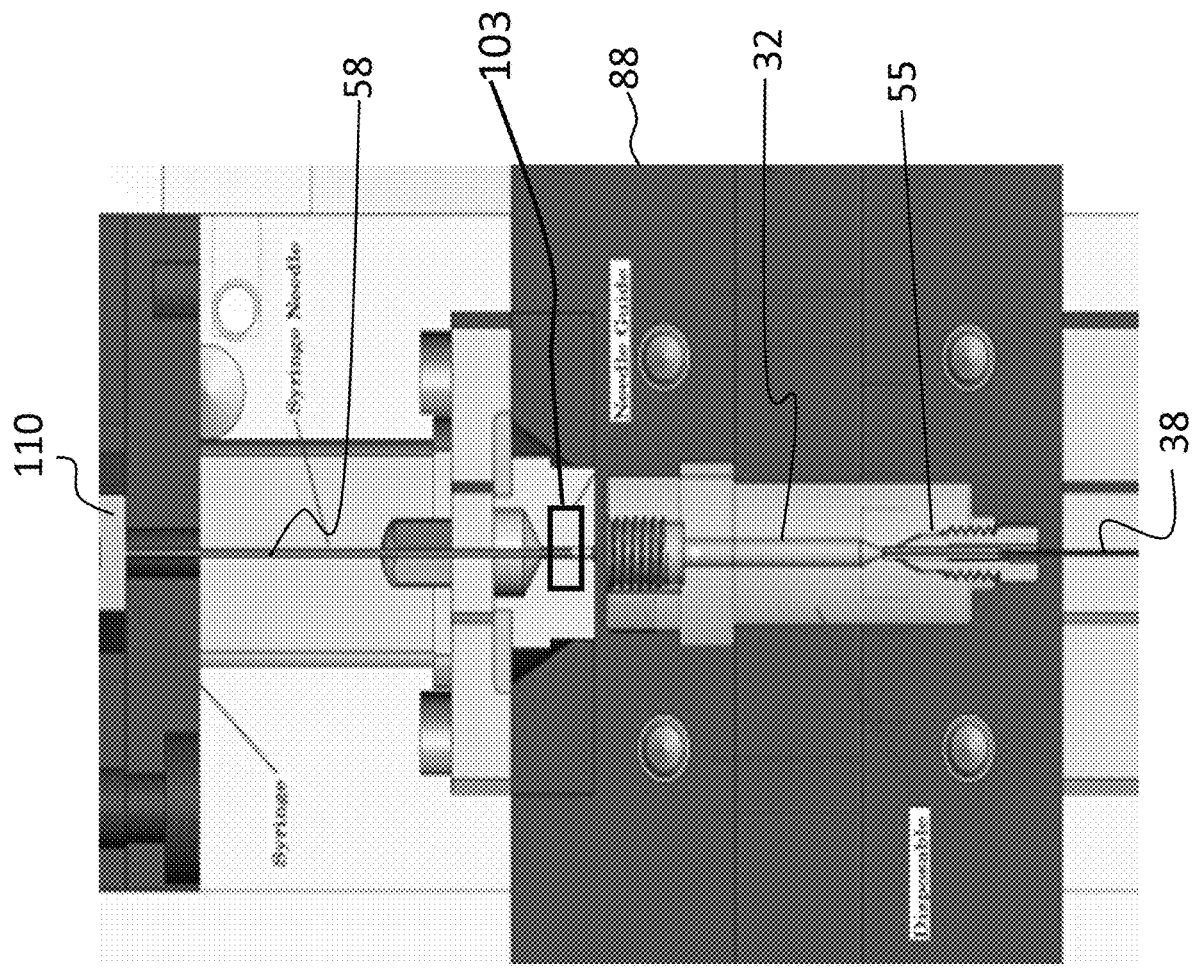
FIG. 5 schematically shows a more detailed cutaway cross-sectional view of a needle and an injection unit.

Referring now to FIG. 5, a more detailed cutaway cross-sectional view of a needle and an injection unit is schematically shown. After the syringe is inserted, the plunger drive plate 82 (as shown in FIG. 4) is lowered until a bead of sample forms at the end of the syringe needle 58. The bead may be cleaned off with lens tissue before proceeding. The drive plate moves slowly because driving the plunger too quickly may crack the syringe seals. The second motor raises the focus cone body holder until the syringe needle tip is recessed in the needle guide. Care must be taken that the needle tip does not protrude beyond the needle guide. The operator may inspect a sensor on a needle locating device 103 to make sure there no contaminants or residue as this can interfere with the measurements or cause cross-contamination.

In operation, the first and second motors cooperatively drive the plunger plate and retract the focus cone body holder to concentrically insert the syringe needle into the sample chamber and control both the needle retraction speed and the sample ejection mass flow so as to create any radially symmetric and axially single-bodied sample profile desired. For example, in operation the amount of sample dispensed during a micro step is proportional to the syringe needle cross-sectional area and the distance translated by the syringe plunger when depressed or extracted.

Figure 6:
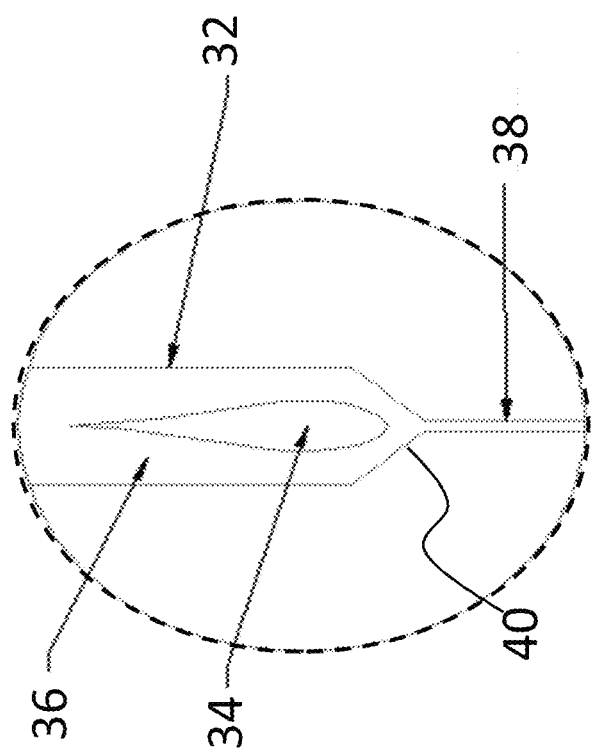
FIG. 6 schematically shows a detailed conceptualized cross-sectional view of a simplified focus cone body.

Referring now to FIG. 6, a detailed cross-sectional view of a conceptualized focus cone body with a precision dispensed sample load shape profile visualized as a tear drop shape in an inner bore is conceptually shown. A sparse volume of sample free optical media 36 shields a plurality of target objects contained in a profile of sample rich optical media 34 within the sample storage region 32 from interfacial points.

Referring now jointly to FIG. 6 and FIG. 7, a cross-sectional view of an example of a focus cone body with a precision dispensed sample load shape profile visualized as a tear drop shape in an inner bore is schematically shown. After sample loading using the precision sample dispenser as described above with respect to FIG. 4, the focus cone body containing the sample and fixedly holding a capillary tube may be mounted for use in an automated optical tomography system such as the Cell-CT™ platform. In that configuration, focus cone body 30 includes a sample storage region 32. When loaded, the sample storage region 32 contains sample rich optical media 34 containing target objects and sheath media region 36. The sheath media region 36, comprises sheath fluid having no target objects, such as, for example, clean/sparse optical oil available commercially as crystal clear Nye® OCF-452H.

The sample storage region 32 has a nozzle 40 fluidly coupled to a capillary tube 38 that is adapted for receiving the optical media 36. Note that the optical media embedded with target objects is deposited in the sample storage region 32 and is conceptually shown as initially having a tear drop profile 34 substantially the same as the calculated load shape profile described above with respect to FIG. 1. As shown, the tear drop load shape profile 34 is a conceptual representation of the sample load shape profile within the sample storage region that is made up of target objects embedded in the optical oil. In one example, the optical oil comprises OCF-452H (Highly viscous). Since both tear drop load shape profile 34 and sheath media 36 are comprised of optical oil, this region can also be considered the volume in which target objects reside.

The focus cone body 30 has an upper threaded bore 42 and a lower threaded bore 44. The upper threaded bore 42 is adapted to receive energizer nut 52. The lower threaded bore 44 has an opening adapted to receive threaded capillary ferrule 54. The focus cone body 30 advantageously includes rim 62 adapted to hold the focus cone body in place when in use by locking into features on a mating CCT part which locks the chamber into place and assures a good seating.

The focus cone nozzle 40 is located where the sample storage region 32 narrows to the diameter of the capillary tube 38. The ferrule 54 functions as a compression fitting to hold the capillary 38 in place. The energizer nut 52 functions to either energize the O-ring 66 and form a kinetic seal against the drive pin 59 or hold a spring-loaded cup seal called a bal-seal (not pictured to simplify the drawing—it may be used in place of an O-ring in an alternative embodiment) in place which naturally forms a kinetic seal with the reciprocating and rotating drive pin 59. Both configurations functionally serve the same purpose: to create a seal between the sample storage region 32, O-ring 66 and nut 52. This fluidically isolates the storage chamber from the atmosphere. In one example, the drive pin 59 is a solid rod with diameter of 2 mm. One end 61 of the drive shaft 59 is on the pressure side of the seal. In one example, the edge is slightly rounded to avoid damaging the seal during assembly. The focus cone body may advantageously be used as a disposable assembly that is a self-encapsulated microfluidic pump fluidically isolated from atmospheric pressure. By applying force on the drive pin, pressure is generated in the storage region. The drive pin 59 is a reciprocating and rotating solid shaft used to control motion of target objects in the capillary tube.

In one example, the focus cone body 30 may advantageously be made of Radel® polyphenylsulfone (PPSU). The sample storage region, also referred to as the "inner diameter" or "inner bore", is, in one useful example, approximately 2 mm in diameter with a slight (e.g. 3 degree) taper. The capillary ferrule 54 similarly has a channel 55 sized to fixedly retain a capillary tube 38. In one example, the capillary tube 38 may comprise a glass capillary tube, having an ID of about 61 microns, and an OD of about 297 microns. In one useful embodiment, the focus cone body 30 including the sample storage region 32, reciprocating drive pin 59 and capillary tube 38 are linearly aligned along a capillary axis 70.

Still referring to FIG. 7, the focus cone body may be used as a disposable self-encapsulated microfluidic pump for containing and subsequently dispensing a preloaded sample. As a disposable, the focus cone body includes the sample storage region having a sheath media region, where the sample storage region is adapted to hold the preloaded sample within the sheath media region and has a nozzle at a dispensing end. The seal and nut cooperate to seal the reciprocating drive pin within the nut, aligned with the nozzle and located at one end of the focus cone body to apply pressure to the sample storage region when activated in a forward direction, where the nut forms a kinetic seal against the drive pin. A fitting holds the capillary tube aligned with the nozzle, where the capillary tube is adapted to receive the preloaded sample from the storage region when the drive pin is actuated in a forward direction.

In one example, the focus cone body is adapted to be preloaded with a selected load shape profile so as to provide for a constant delivery of a sample from the sample chamber to an imaging zone within a capillary tube.

In another example, the preloaded sample has a tear drop load shape profile proportional to a pre-calculated load shape profile.

In another example, the storage region is adapted to reverse the flow of the preloaded sample from the capillary tube the when the drive pin is actuated in a reverse direction.

In another example, the drive pin comprises a reciprocating and rotating solid shaft used to control motion of target objects in the capillary tube.

In another example, the selected load shape profile comprises a substantially tear-shaped load shape profile.

In another example, the sample storage region is adapted to be pre-loaded by a syringe.

In another example, the sample storage region comprises a generally cylindrical channel that tapers down at the nozzle end.

In another example, the focus cone body, drive pin and capillary tube are adapted to mate with an optical system.

Of the many methods for positioning the sample fluid within the sheath fluid in the chamber several examples can be hypothesized including, but not limited to, the following:
1. Simple or complex computational fluidic modeling wherein the sample is deposited into a chamber pre-filled with clean optical oil via a needle inserted from the top of the chamber.
2. Simple or complex computational fluidic modeling wherein the Prepjet™ device is loaded from the exit port— using the modeled sample prediction as a template the fluid is dispensed from a fine hypotube inserted in the fluid exit port.
3. Reversible flow loading: Here the drive-pin is synchronously retracted by the same volume as the sample while the dispenser injects a coaxial sheath and sample from the exit port. Each sample is then reversed when the chamber drive-pin is pressed and flow is driven through an imaging capillary.

In this way, a preloaded coaxial sample and sheath combination that has near optimal time of flight for the sample can be transferred from a sample chamber to the imaging zone within the capillary. The core size for sample within the sheath can be tailored to optimize performance in an imaging flow cytometer. Small sheath volumes will maximize target object throughput, however, other variables that affect flow cytometer performance such as clogging or center-biased imaging regions can be influenced beneficially by increasing sheath fluid volume. The most effective sheath-sample ratio will be application specific.

Figure 8:
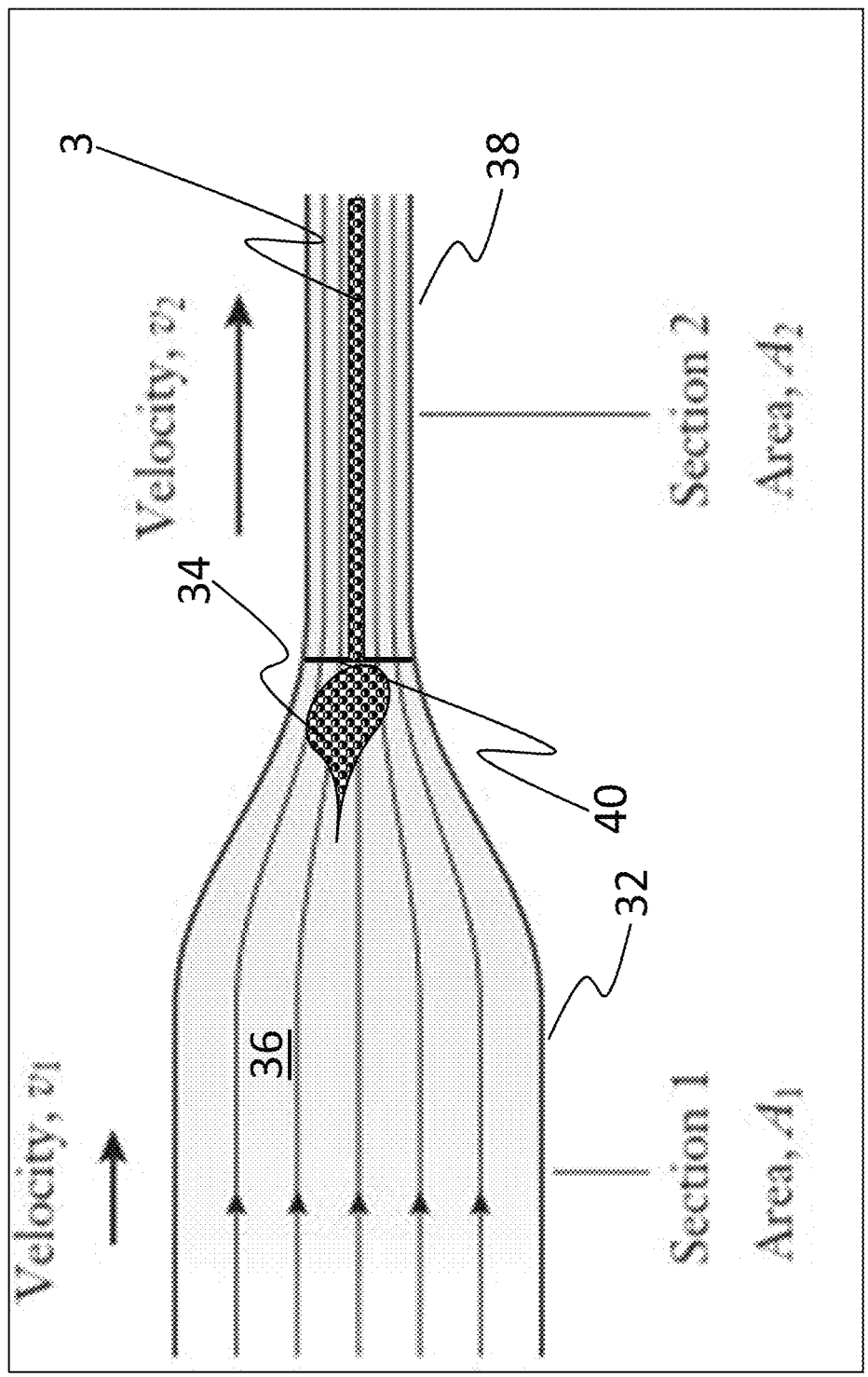
FIG. 8 schematically illustrates the laminar flow effect resulting from depositing a substantially optimal load shape into a focus cone body chamber.

Referring now to FIG. 8, a laminar flow effect resulting from depositing a substantially optimal load shape into a focus cone body chamber is schematically illustrated. In order to predict fluid motion, it is advantageous to use a method of hydrodynamic focusing where objects are suspended in extremely viscous oil. Suspension in such viscous oil allows pre-positioning of objects with negligible object movement due to gravity or inertia. It also allows accurate prediction of fluid motion under pressure. The ability to predict fluid motion enables computational calculation of an "optimal profile," as described above.

The sample rich optical media 34 initially resides in the sample storage region 32 surrounded by sample free optical media 36. A plurality of objects 3 are contained in the sample rich optical media 34. As the plurality of objects 3 are dispensed into the capillary tube 38 parallel layers of non-mixing fluid form in a manner characteristic of laminar flow. Laminar flow ensures deterministic and predictable motion of the sample from the focus cone body, into the capillary and ultimately to an imaging plane. Advantages of the load shape profile in the sheath media include a decrease in loss of target objects to wall adhesion, a decrease in the prevalence of clogging in the capillary and a decrease in the necessary search volume for a follow-on device such as the Cell-CT™ platform.

Figure 9:
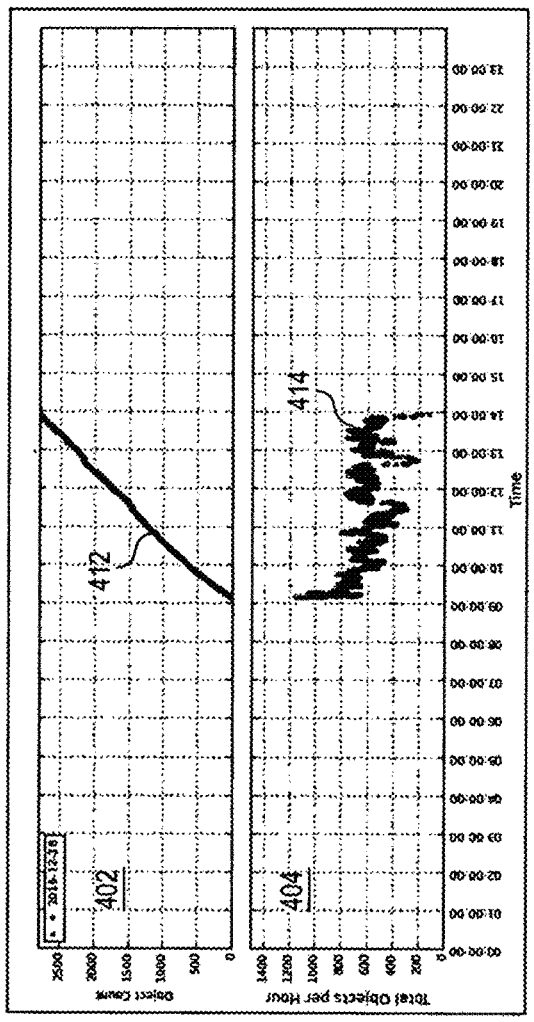
FIG. 9 graphically shows expected throughput from a substantially optimized load shape profile.

Referring now to FIG. 9, an expected throughput from a substantially optimized load shape profile is graphically illustrated. Plot 402 shows object count on the Y-axis and time in hours on the X-Axis. For a substantially optimized load shape profile, the object count would be expected to increase generally linearly with respect to time as shown in curve 412. Plot 404 shows total objects per hour vs. time and corresponds to the upper plot 402. Each point in curve 414 represents an object. Note that the number of objects counted per hour remains relatively equal over the course of the test. Furthermore, this is illustrated by the linearity of curve 412.

Figure 10:
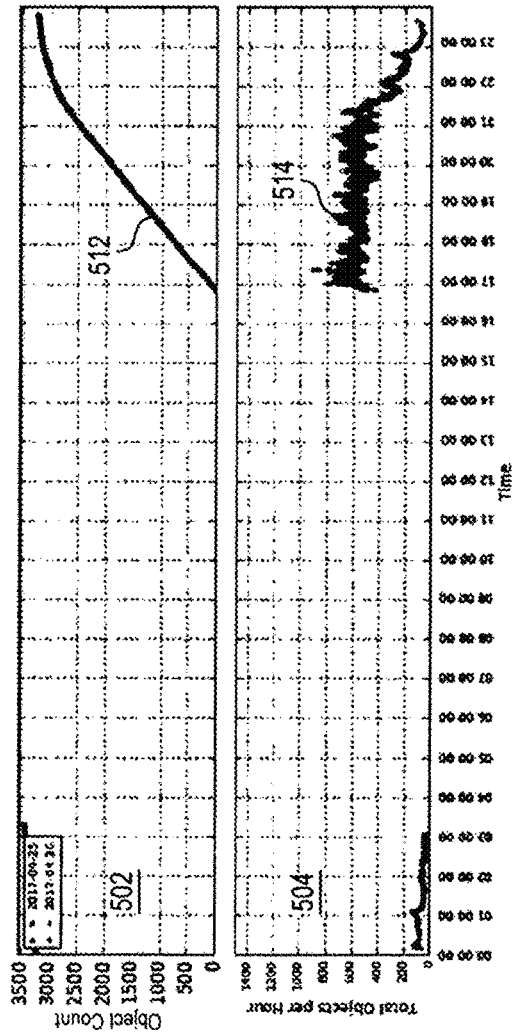
FIG. 10 graphically shows expected throughput from a non-optimized load shape profile.

Referring now to FIG. 10, an expected throughput from a non-optimized load shape profile is graphically illustrated. Plot 502 shows object count on the Y-axis and time in hours on the X-Axis. In contrast to a substantially optimized load shape profile, the object count would be expected to increase generally non-linearly with respect to time as shown in curve 512. Plot 504 shows total objects per hour vs. time and corresponds to the upper plot 502. Each point in curve 514 represents an object. Note that the number of objects counted steadily decreases with time. As expected, curve 512 exhibits a decaying slope.

Figure 11:
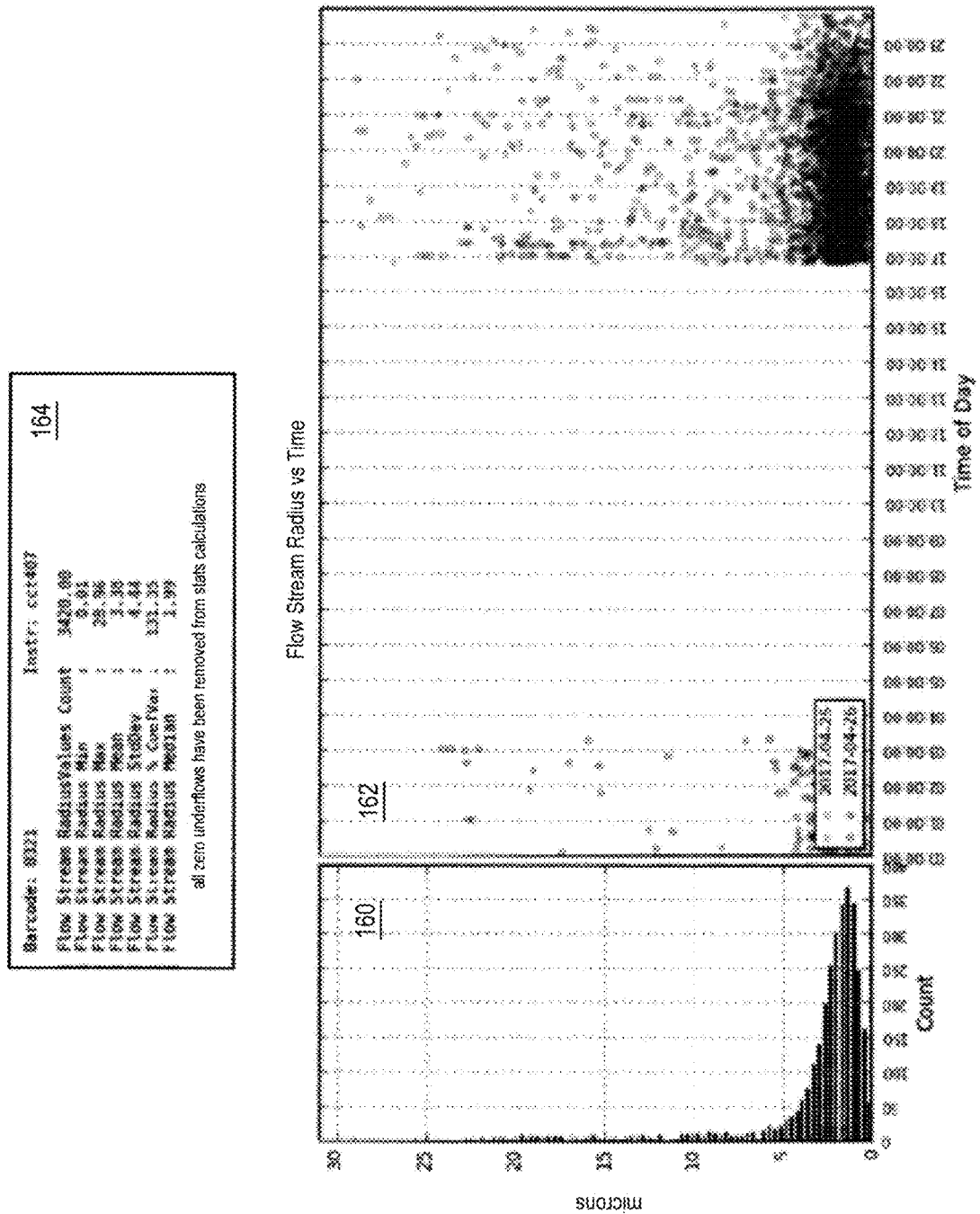
FIG. 11 graphically shows the object radii from a sample run where 90% of the objects fell between 0 and 15 um.

Referring now to FIG. 11, object radii from a sample run where 90% of the objects fell between 0 and 15 um is graphically illustrated. A first plot 160 is a histogram that includes a Y-axis representing object radii in microns as measured from the center of a capillary tube and an X axis representing a count of the number of objects at the measured radii. The total count as shown in the table 164 is 3420 objects. The minimum radius was measured at 0.01 µm, the maximum radius was measured at 28.96 µm and the mean measured at 3.38 µm with a standard deviation of 4.44 µm. For the set of measurements, the percentage of coefficient variance was 131.35 and the radius median was 1.99 µm. All zero underflows have been removed from the statistical calculations.

Here plotted is the flow stream radius on the Y-axis vs. time on the X-Axis. The data points each represent a single object counted at the corresponding time. A second plot 162 is a representation of the histogram of plot 160 shown in a different form.

Figure 12:
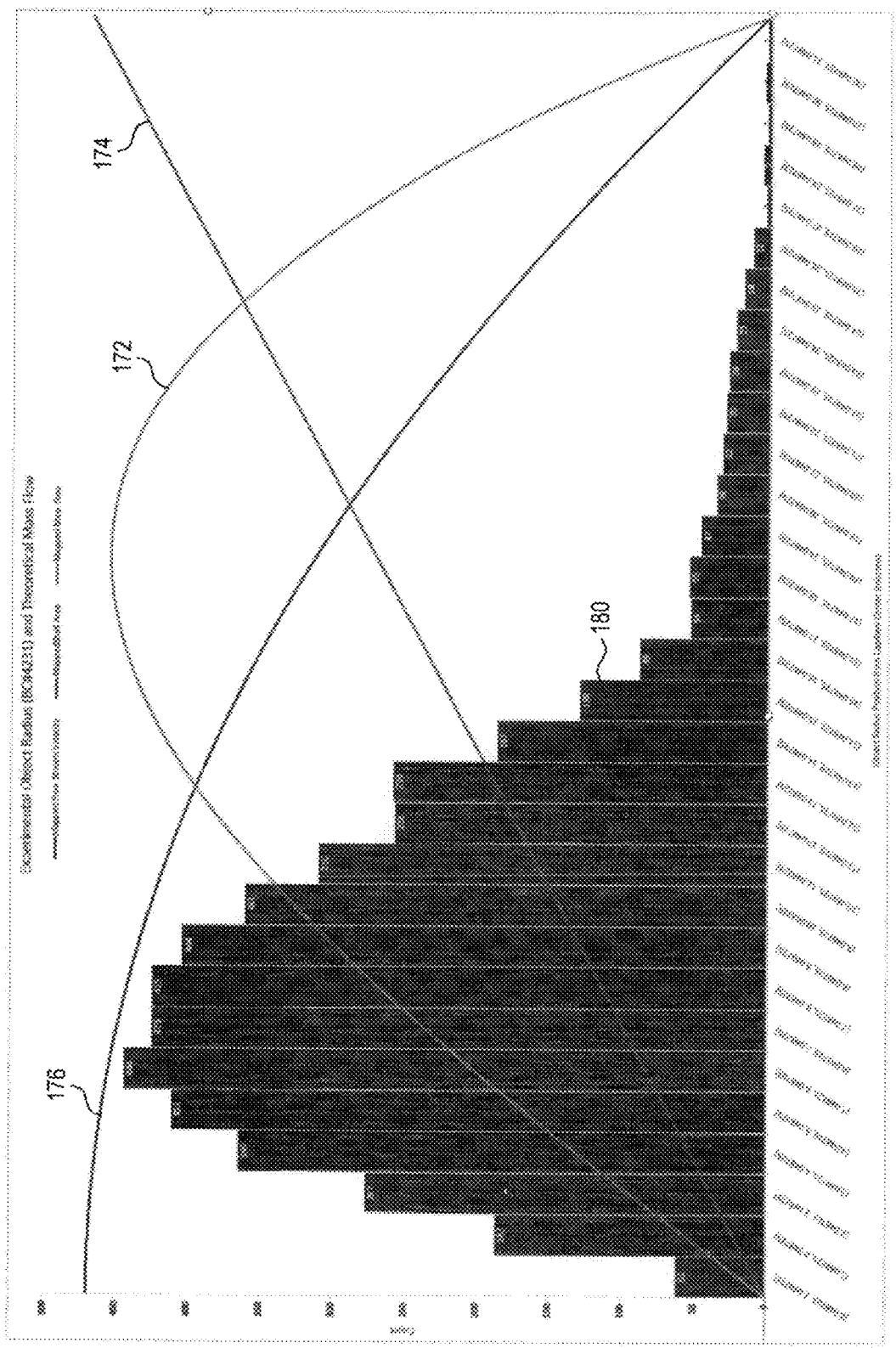
FIG. 12 graphically shows the theoretical mass flow of a non-optimized/homogenous load shape profile overlaid on the histogram of experimental object radius data from an optimally loaded Prepjet™ device.

Referring now to FIG. 12, theoretical mass flow of the flow of all fluid moving through a chamber and capillary is graphically illustrated. Here the X-axis represents capillary radius as measured in microns and the Y-axis is a normalized axis corresponding to object count. The theoretical mass flow of a non-optimized/homogenous load shape profile (Bottom Loaded) is represented by curve 172. Curve 176 represents the flow stream velocity of objects in µm per second. Curve 174 represents the area of concentric rings at each bin radius. The mass flow value 172 is proportional to area multiplied by the flow rate, in other words, 172 is proportional to the product of 176 and 174. Any distribution more weighted towards the center is indicative of dynamic focusing and a metric of an effective load. Histogram 180 represents the count of object radius position from the capillary tube center in microns.

Still referring to FIG. 12, it can be seen that at a capillary radius of about 5 µm the flow rate is near its peak value. At the same time, the area is approaching 0, as is the mass flow. Comparing with this theoretical optimization with the actual example plotted in FIG. 1, it can be seen that the pre-positioning technique system is functioning to hydrodynamically focus target objects since the highest count of objects is centered around radius of 5 µm.

In order to promote better understanding of the system and method disclosed herein, an example of the system operation will now be described in detail. In one example, the following parameters applied. In this example, the sheath media was optical media with an index of refraction matching the index of refraction of the subsequent viewing optics. The optical media was OCF-452H. The sample was prepared as described above before implementing the following process.

1. A 100 microliter syringe having a 22s-gauge needle was filled with 30 microliters of sample and mounted in the injection device.

2. A focus cone body including 50 microliters of sheath fluid in the sample was mounted in the injection device to receive the sample from the syringe. The chamber size was 16*pi cubic microliters. The syringe nozzle diameter was 370 microns.

3. Motor 2 operated to position the syringe needle at the bottom of the Prepjet™ device inner chamber, directly above the nozzle.

4. The syringe plunger was pressed by operation of the first motor to begin dispensing the sample into the focus cone body chamber at a consistent rate 5. The focus cone body was withdrawn by operation of the second motor while the sample is being dispensed by step 4. The rate of focus cone body retraction is mediated by the second motor and determines the shape of deposited sample.

6. After removal from the injection device, the loaded focus cone body was viewed using a Cell-CT™ platform and the objects counted.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

What is claimed is:

1. A method for pre-positioning a fluid sample in a sheath fluid for dispensing a radially symmetric coaxial sheathed sample into a capillary tube installed in an optical tomography system, the method comprising:
    obtaining a fluid sample wherein the sample includes a plurality of objects residing in solution;
    introducing a sheathed fluid into a sample chamber of an injecting device in fluid communication with the capillary tube, wherein the sample chamber comprises
        a focus cone body with an inner bore configured to be preloaded with a sheathed fluid having a selected sample load profile, and
        wherein the selected sample load profile has a substantially tear-drop shape;
    preloading the sample chamber by dispensing the sample into the sample chamber containing the sheathed fluid in steps as a series of cross-sectional slices, each of the series of cross-sectional slices having substantially the same predetermined thickness;
    and
    transferring the preloaded sample into the capillary tube; and
    wherein the selected sample load profile with cross-sectional slices is calculated by a programmed controller connected to a first motor and a second motor further connected to the sample chamber of an injecting device so as to provide laminar fluid flow regime of the sample fluid flow within the sheathed fluid and to define the tear-drop shape of the sample load profile.

2. The method of claim 1 wherein the sheath fluid comprises optical oil.

3. The method of claim 1 wherein the step of loading a sample chamber comprises operating an injection device including a syringe wherein the syringe contains the sample.

4. The method of claim 1 wherein the plurality of objects comprise biological cells.

* * * * *